United States Patent
Fimreite

(10) Patent No.: US 8,412,799 B2
(45) Date of Patent: Apr. 2, 2013

(54) METHOD AND SYSTEM FOR COMMUNICATION USING A MEDICAL IMAGING PROTOCOL

(76) Inventor: Svein Fimreite, Horten (NO)

( * ) Notice: Subject to any disclaimer, the term of this patent is extended or adjusted under 35 U.S.C. 154(b) by 196 days.

(21) Appl. No.: 12/959,409

(22) Filed: Dec. 3, 2010

(65) Prior Publication Data

US 2011/0302268 A1 Dec. 8, 2011

(30) Foreign Application Priority Data

Apr. 6, 2010 (NO) .................................. 20100488

(51) Int. Cl.
*G06F 15/16* (2006.01)
(52) U.S. Cl. ........................................................ 709/217
(58) Field of Classification Search .................... 709/217
See application file for complete search history.

(56) References Cited

U.S. PATENT DOCUMENTS

| | | | |
|---|---|---|---|
| 2007/0118635 A1* | 5/2007 | Nakano | 709/223 |
| 2009/0125541 A1 | 5/2009 | Amon | |
| 2009/0125816 A1 | 5/2009 | Amon | |
| 2009/0164253 A1* | 6/2009 | Lyshkow | 705/3 |

OTHER PUBLICATIONS

Digital Imaging and Communications in Medicine (DICOM), Part 4: Service Class Specifications Published by National Electrical Manufacturers Association, 2008.
Digital Imaging and Communications in Medicine (DICOM), Part 7: Message Exchange Published by National Electrical Manufacturers Association, 2008.
Strategic Document, Digital Communications in Media and Medicine, Oct. 25, 2010.
Digital Imaging and Communications in Medicine From Wikipedia, the free encyclopedia, Oct. 22, 2010.

* cited by examiner

*Primary Examiner* — John Follansbee
*Assistant Examiner* — Zakaria Zouaki
(74) *Attorney, Agent, or Firm* — Christian D. Abel

(57) ABSTRACT

A method for communication between a DICOM QR-enabled device, such as a medical imaging device, and a DICOM QR-enabled computer. The method includes transferring, using the DICOM QR protocol, an explicit command from the DICOM QR-enabled device to the DICOM QR-enabled computer. The DICOM QR-enabled device may include a user interface, and the explicit command may have been received in advance from a user through the user interface. The explicit command may be a question or a command to perform a task that is otherwise unavailable for medical imaging devices. The command may include at least one parameter.

7 Claims, 3 Drawing Sheets

METHOD AND SYSTEM FOR COMMUNICATION USING A MEDICAL IMAGING PROTOCOL

FIELD OF THE INVENTION

Embodiments of the invention relate to data communication using a medical imaging protocol. More particularly, embodiments of the invention relate to a system and method for communication between a DICOM QR-enabled device and a DICOM QR-enabled computer.

BACKGROUND

Digital Imaging and Communications in Medicine (DI-COM) is a standard for e.g. handling and transmitting medical imaging information. It includes a file format definition and a network communications protocol. The communication protocol is an application protocol that uses TCP/IP to communicate between systems. DICOM files can be exchanged between entities that are capable of receiving image and patient data in DICOM format.

DICOM provides different services, most of which involve transmission of data over a network. One such service is query and retrieve (DICOM-QR), which enables a workstation or another DICOM QR-enabled device to find lists of images or other objects and then retrieve them from a remote unit such as a PACS, or another DICOM QR-enabled computer.

DICOM-QR is therefore commonly used in cases where patient images and data are transferred.

The DICOM-QR has, however, certain limitations. Usually, a user interface provided on a DICOM QR-enabled device allows a user to enter data specifically adapted to the query-retrieve service, e.g., the user ID of a patient.

It would be useful to provide extended functionality through the DICOM QR-enabled device's user interface.

SUMMARY OF THE INVENTION

In an aspect the invention provides a method for communication between a DICOM QR-enabled device and a DICOM QR-enabled computer, including transferring, using the DICOM QR protocol, an explicit command from the DICOM QR-enabled device to the DICOM QR-enabled computer.

In another aspect the invention provides a method performed by a DICOM QR-enabled computer communicatively interconnected with a DICOM QR-enabled device, including receiving, using the DICOM QR protocol, an explicit command from the DICOM QR-enabled device.

In still another aspect the invention provides a DICOM QR-enabled computer, communicatively interconnected with a DICOM QR-enabled device, the DICOM QR-enabled computer including a processor and a memory containing computer program instructions, the computer program instructions being configured to cause the DICOM QR-enabled computer to receive, using the DICOM QR protocol, an explicit command from the DICOM QR-enabled device.

Further embodiments have been disclosed in the appended dependent claims.

Still further aspects and embodiments will be more fully understood from the following detailed description and the drawings.

DETAILED DESCRIPTION

Figure 1:
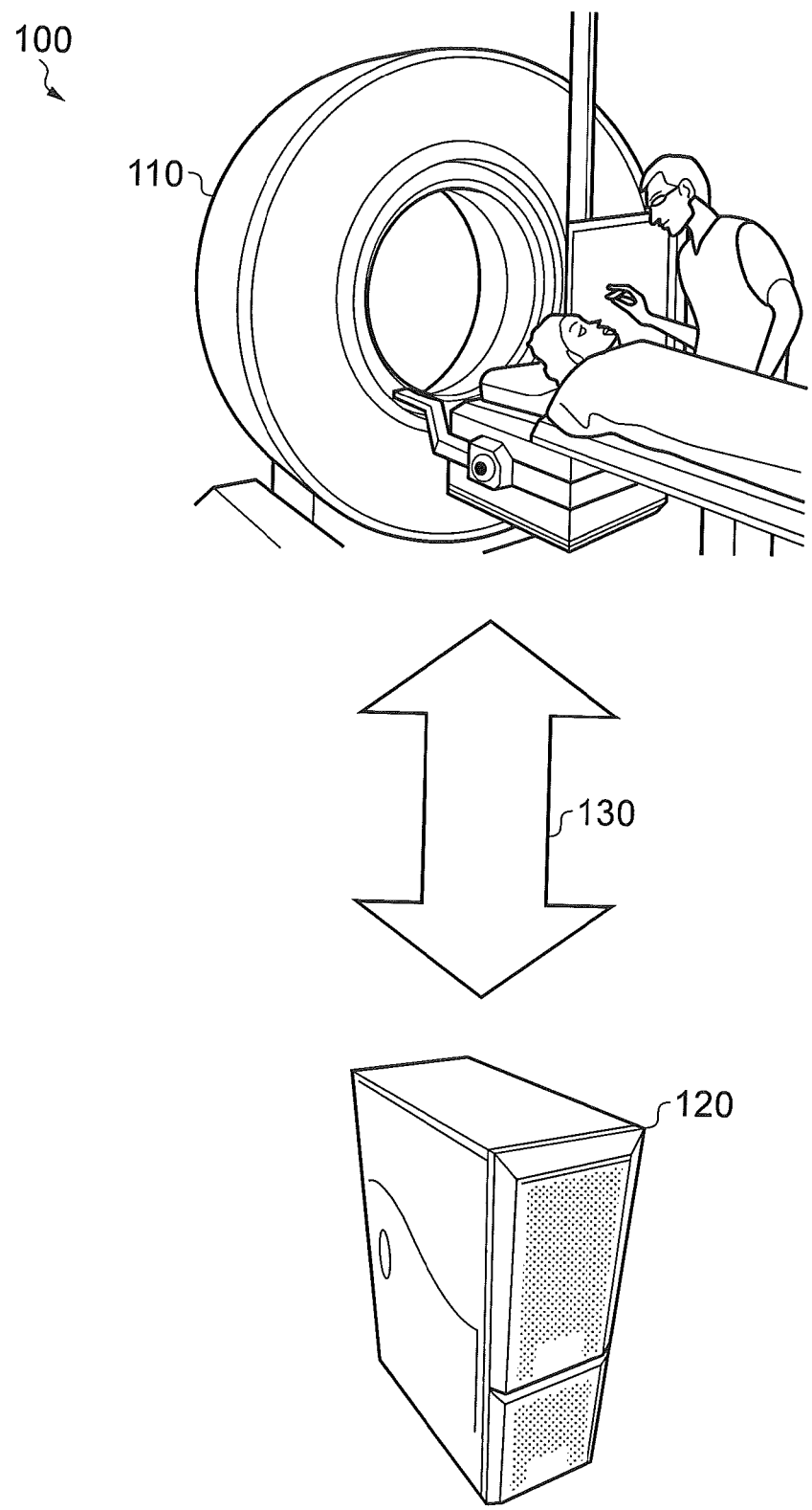
FIG. 1 is a schematic block diagram illustrating basic elements included in a DICOM QR system.

FIG. 1 is a schematic block diagram illustrating basic elements included in a DICOM QR system.

The system 100 includes a DICOM QR-enabled device 110 and a DICOM QR-enabled computer 120 which are communicatively interconnected via a bidirectional communication connection 130.

The DICOM QR-enabled device 110 may include a user interface, although this has not been illustrated in FIG. 1. Such a user interface may include a display, a keyboard, and/or various user input devices such as a mouse, pointing tool, touchpad, etc, and associated circuits and processing devices.

In an aspect the DICOM QR-enabled device 110 may be a DICOM QR-enabled medical imaging device. More specifically, such a device may be an imaging device within one of the product segments X-ray, computed tomography, ultrasound, magnetic resonance imaging, positron emission tomography, PACS, RIS or nuclear imaging. The imaging device may be diagnostic imaging equipment such as a scanner. As an alternative, the DICOM QR-enabled device 110 may be a workstation, including an operator console, a terminal, etc.

The DICOM QR-enabled computer 120 may be a dedicated computer supporting explicit commands as disclosed herein.

The DICOM QR-enabled computer 120 may alternatively be a workstation or a PACS, etc., supporting explicit commands as disclosed herein.

The communication connection 130 between the DICOM QR-enabled device 110 and the DICOM QR-enabled computer 120 may be any communication connection included in a data communication network supporting the DICOM specification. Such networks may include wired and wireless networks and sub-networks, and intermediate network elements such as routers, switches, bridges, hubs and gateways, which operate according to TCP/IP protocol. Appropriate networks include at least one of a local area network, a wide area network, a global network such as the Internet.

It will be understood that FIG. 1, for illustration purposes, shows the simplest possible configuration of one DICOM QR-enabled device 110 communicatively connected to one DICOM QR-enabled computer 120. It should be recognized that in other embodiments, one or a plurality of DICOM QR-enabled devices 110 and one or a plurality of DICOM QR-enabled computers 120 may be communicatively interconnected.

It should be recognized that the DICOM QR-enabled device 110 and the DICOM QR-enabled computer 120 may be localized in close proximity to each other, such as in the same room or building (e.g., a hospital), or remotely with respect to each other, such as in different buildings (e.g., hospitals) or even in different geographical areas or regions, dependent on circumstances.

Figure 2:
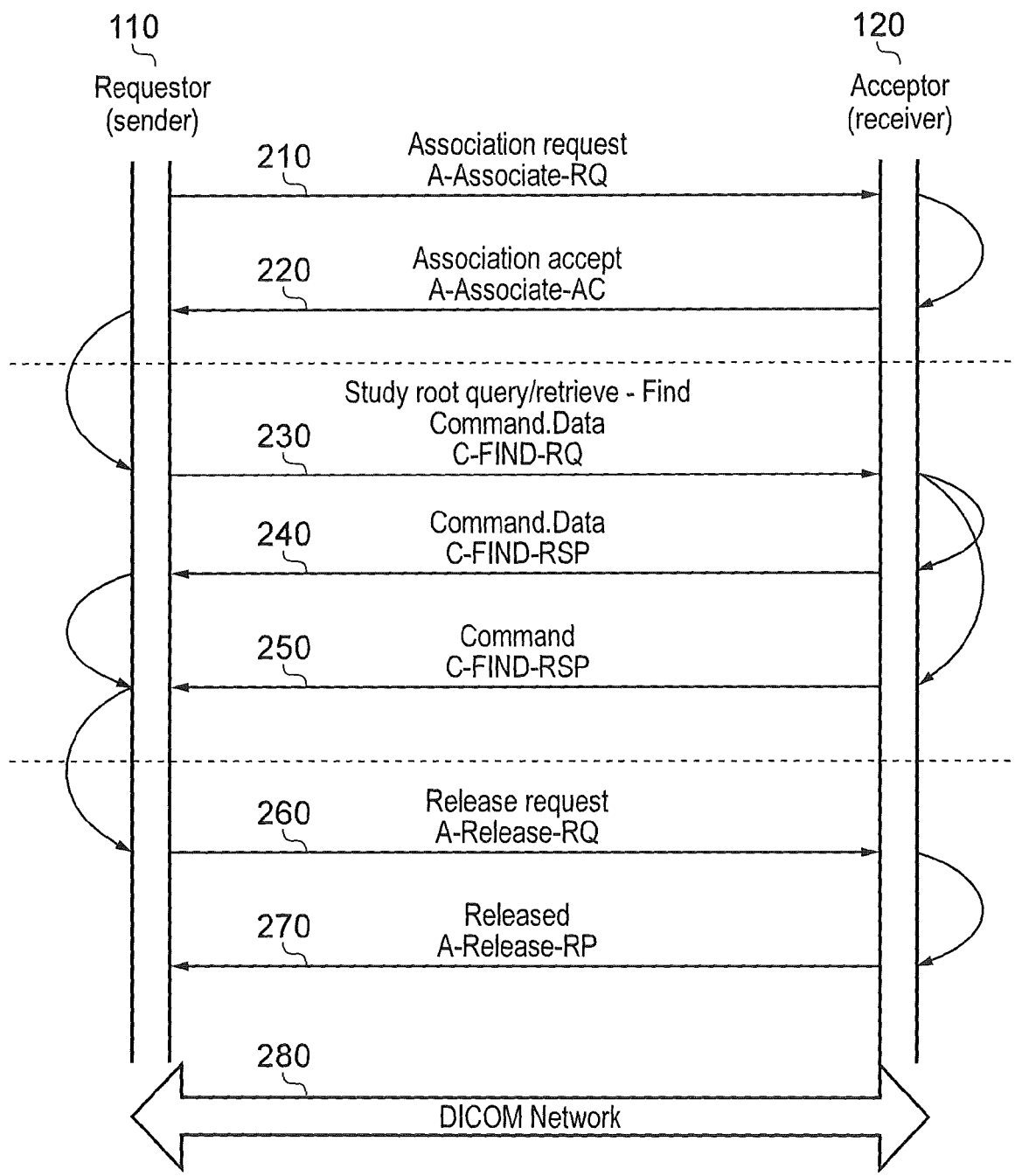
FIG. 2 is a schematic time chart illustrating an exemplary communication between a DICOM QR-enabled device and a DICOM QR-enabled computer.

FIG. 2 is a schematic time chart illustrating an exemplary communication between a DICOM QR-enabled device 110 and a DICOM QR-enabled computer 120. All communications steps are performed over the DICOM network, as illustrated at 280.

For illustration purposes, in FIG. 2, the DICOM QR-enabled device 110 has been denoted "Requestor (sender)" and a DICOM QR-enabled computer 120 has been denoted "Acceptor (receiver)".

First, in step 210, an association request is submitted from the DICOM QR-enabled device 110. The association request is received by the DICOM QR-enabled computer 120.

Next, in step, 220, an association accept is submitted from the DICOM QR-enabled computer 120. The association accept is received by the DICOM QR-enabled device 110.

Next, in step 230, a study root query/retrieve-find command data (C-FIND-RQ) is submitted from the DICOM QR-enabled device 110 and received by the DICOM QR-enabled computer 120. C-FIND-RQ includes the current explicit command. In response to the receipt, the DICOM QR-enabled computer 120 interprets and executes the requested explicit command.

If the explicit command was a question, the execution of the explicit command may result in an answer to the question.

If the explicit command was not a question, the execution of the explicit command may result in a summary of the execution.

As a result, command data (C-FIND-RSP) is submitted by the DICOM QR-enabled computer 120 and received by the DICOM QR-enabled device 110. The submission of command data may be separated into two operations, denoted steps 240 and 250 respectively. The command data includes output which may be an answer if the explicit command was a question, or otherwise a summary of current execution.

Next, in step 260, a release request (A-Release RQ) is submitted by the DICOM QR-enabled device 110.

As a result, a release acknowledgement (A-Release-RP) is submitted by the DICOM QR-computer 120 in step 270.

Figure 3:
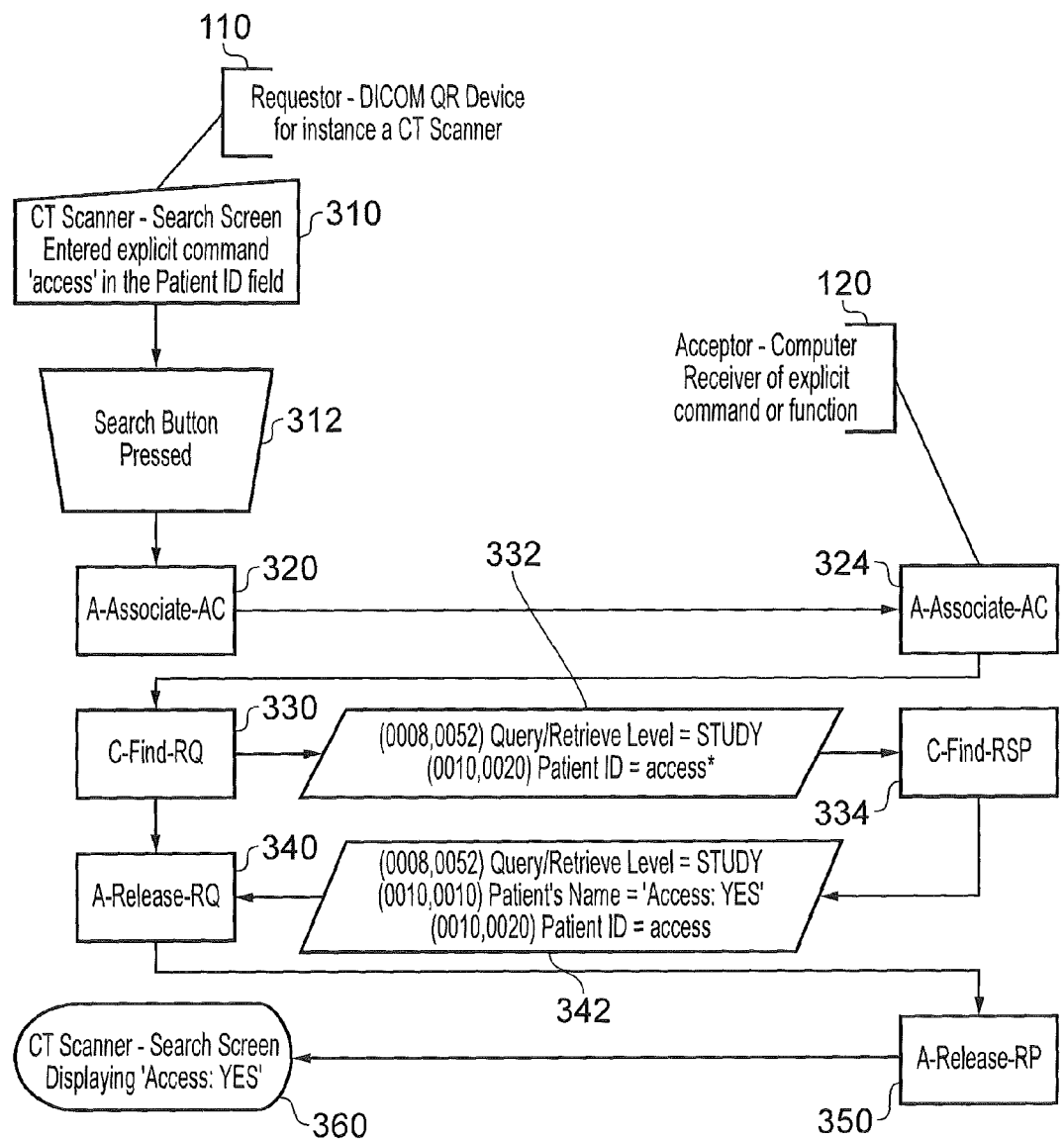
FIG. 3 is a schematic flow chart illustrating an exemplary communication between a DICOM QR-enabled device and a DICOM QR-enabled computer.

FIG. 3 is a schematic flow chart illustrating another exemplary communication between a DICOM QR-enabled device 110 and a DICOM QR-enabled computer 120.

In this example, for illustrative purposes and not for limitation, it is assumed that the DICOM QR-enabled device is a CT scanner.

In step 310, at the CT scanner, a search screen is displayed on the display of the CT scanner's user interface. The search screen includes a patient ID field, which is regularly used for entering search criteria such as an identification of a patient.

However, according to the invention the patient ID search field is changed into an explicit command user interface. An explicit command, such as the command "access", is entered by the user in the patient ID field in step 310.

In order to terminate the entering of the explicit command, the user presses a search button in step 312. It should be recognized that the pressing of a search button may include user action such as clicking on a mouse button or another pointing tool button, pressing an enter key, pressing a function key, or any other appropriate user action indicating that the explicit command has been entered.

In step 320, an association request is submitted from the DICOM QR-enabled device 110. The association request is received at the DICOM QR-enabled computer 120 in the receiving step 324. As a result, in step 324, the DICOM QR-enabled computer 120 submits an association accept back to the DICOM QR-enabled device 110. Such association handshaking corresponds substantially to steps 210 and 220 described with reference to FIG. 2.

Then, in step 330, a C-Find-RQ 332 is submitted from the DICOM QR-enabled device 110. The Query Retrieve Level and the explicit command are included in C-Find-RQ.

More specifically, in this example, the explicit command "access" is stored in DICOM TAG (0010, 0020) Patient ID in C-Find-RQ. In alternative examples, the Query Retrieve Level may be STUDY and may in certain embodiments be selected from either PATIENT, STUDY, SERIES or IMAGE.

In step 334 command data (C-FIND-RSP) 342 is submitted by the DICOM QR-enabled computer 120 to the DICOM QR-enabled device 110.

In step 340 a release request (A-Release RQ) is submitted by the DICOM QR-enabled device 110. As a result, a release acknowledgement (A-Release-RP) is submitted by the DICOM QR-computer 120 in step 350.

The illustrated process in FIG. 3 is terminated at step 360.

In the illustrated example shown in FIG. 3, the explicit command was an "access" command, such as an "INETAccess" command. This is a command for checking internet access or otherwise a connection/communication status between the DICOM-enabled computer 120 and an external communication network such as the Internet. It should be understood that such a command is an example of the explicit command being a question. The output, or result, of such a command may be an answer of the question. In this example the output or result may be a binary or logic quantity representing either "YES" or "NO".

In other embodiments the explicit command may be a command with at least one parameter, to perform tasks that are otherwise unavailable for medical imaging devices. An example of such a command is a message transmission command for initiating transmission of a message from the DICOM-enabled computer 120 to an external communication device which is communicatively connected to the DICOM-enabled computer 120, e.g. via intermediate network elements, including wireless connections. The external communication device may, e.g., be a mobile telephone or another portable wireless communication device, which is enabled for receiving a message initiated and submitted by the DICOM-enabled computer 120. In such a case, the explicit command may be a message transmission command, such as a "SendSMS(mobilenumber, message)" command for sending an SMS to a particular mobile number. The mobile number and message (message content) may be parameters to the SendSMS command. The output (result) of the execution of the explicit command may in this case include a summary of the operation, such as "SMS successfully sent" or "SMS failed"

In still other embodiments the explicit command may be a command without such parameters, again for performing tasks that are otherwise unavailable for medical imaging devices. An example of such a command is a clear command for clearing a current delivery of patient image(s). Another example is a count command for retrieving a number of patient image deliveries, such as a "DeliveryCount" command to get numbers of patient image deliveries. The output (result) of the execution of the explicit command may in such a case be a counting number.

In summary, certain aspects of the disclosed invention makes it possible to send an explicit command with existing systems and products that support the DICOM QR protocol, without the need for installation of new software in the DICOM QR-enabled device. Also, there is no or minimal need for special training of personnel on a new graphical user interface.

Further, certain aspects of the disclosed method make it possible to control other tasks designated by the use of C-FIND in the DIMSE-C group in the DICOM-QR.

DIMSE is an abbreviation for DICOM Message Service Element, DIMSE-C is a DICOM Message Service Element (DIMSE) used for a composite information object, and C-FIND is a particular DIMSE-C service.

Certain aspects of the disclosed method provide a procedure that is simple and cost effective in both implementation and use. The method may utilize existing infrastructure and equipment, and may provide a procedure that makes it easy for users to perform new and desired operations, based on an explicit command or function.

The method has been described with reference to certain embodiments and examples. It will be understood by those skilled in the art that various modifications and variations may exist within the scope of the appended claims.

The invention claimed is:

1. Method for executing a function by a DICOM QR enabled device that is a non-native function of the device using the DICOM QR protocol, comprising the steps of:
   a. Entering a command in a data field in a user interface on the DICOM QR enabled device, said command relating to a function not native to the device,
   b. Communicating an association-request command using the DICOM QR protocol via TCP/IP from the device to a DICOM QR enabled computer,
   c. Communicating an association-accept command from the computer to the device,
   d. Communicating a root query/retrieve C-FIND-RQ data command from the device to the computer, the root query/retrieve C-FIND-RQ data command comprising the non-native command entered into the data field,
   e. Interpreting the non-native command in a program installed on the DICOM enabled computer, said program arranged to interpret and execute said non-native command,
   f. Executing the command on the DICOM enabled computer,
   g. Communicating a root query/retrieve C-FIND-RSP data command from the computer to the device, the root query/retrieve C-FIND-RSP data command comprising the result from the execution of the non-native command,
   h. Communicating a release request command from the device to the computer,
   i. Communicating a released command from the computer to the device, and
   j. Displaying the result from the execution of the non-native command in a user interface on the DICOM QR enabled device.

2. Method according to claim 1 wherein non-native command is stored in a DICOM TAG.

3. Method according to claim 2, wherein the DICOM TAG is a part of the content of the root query/retrieve C-FIND-RQ.

4. Method according to claim 3, wherein the root query/retrieve C-FIND-RQ is at a PATIENT, STUDY or IMAGE level.

5. Method according to claim 1, wherein the DICOM QR-enabled device is a medical imaging device.

6. Method according to any of claims 1-5, wherein the non-native function is the ability to access an external communications network.

7. Method according to claim 6, wherein the external communications network is the Internet.

* * * * *